United States Patent
Lee et al.

(10) Patent No.: US 11,351,519 B2
(45) Date of Patent: Jun. 7, 2022

(54) ABSORBENT POLYMERS, AND METHODS AND SYSTEMS OF PRODUCING THEREOF AND USES THEREOF

(71) Applicant: Novomer, Inc., Boston, MA (US)

(72) Inventors: Han Lee, Chicago, IL (US); John B. Ruhl, Rochester, NY (US); Robert E. Lapointe, Syracuse, NY (US); Kyle Sherry, Somerville, MA (US); Alexander Tseitlin, Acton (CA); Sadesh H. Sookraj, Cambridge, MA (US)

(73) Assignee: Novomer, Inc., Rochester, NY (US)

( * ) Notice: Subject to any disclaimer, the term of this patent is extended or adjusted under 35 U.S.C. 154(b) by 511 days.

(21) Appl. No.: 16/346,853

(22) PCT Filed: Oct. 31, 2017

(86) PCT No.: PCT/US2017/059249
§ 371 (c)(1),
(2) Date: May 1, 2019

(87) PCT Pub. No.: WO2018/085254
PCT Pub. Date: May 11, 2018

(65) Prior Publication Data
US 2019/0255512 A1    Aug. 22, 2019

Related U.S. Application Data

(60) Provisional application No. 62/416,611, filed on Nov. 2, 2016.

(51) Int. Cl.
| | | |
|---|---|---|
| *C08G 63/08* | (2006.01) | |
| *C07C 51/09* | (2006.01) | |
| *C08G 63/78* | (2006.01) | |
| *A01C 1/06* | (2006.01) | |
| *A01N 25/34* | (2006.01) | |
| *B01J 20/26* | (2006.01) | |
| *A61L 15/24* | (2006.01) | |
| *B01D 3/14* | (2006.01) | |
| *B01J 19/00* | (2006.01) | |
| *B01J 19/06* | (2006.01) | |
| *B01J 19/24* | (2006.01) | |
| *B01J 20/30* | (2006.01) | |
| *C08G 81/02* | (2006.01) | |
| *C08G 63/91* | (2006.01) | |
| *C08F 120/06* | (2006.01) | |
| *C07C 51/44* | (2006.01) | |
| *C08F 220/06* | (2006.01) | |
| *C07D 305/12* | (2006.01) | |
| *C08G 63/83* | (2006.01) | |
| *A01C 21/00* | (2006.01) | |

(52) U.S. Cl.
CPC ........... *B01J 20/264* (2013.01); *A01C 1/06* (2013.01); *A01N 25/34* (2013.01); *A61L 15/24* (2013.01); *B01D 3/14* (2013.01); *B01J 19/0013* (2013.01); *B01J 19/06* (2013.01); *B01J 19/245* (2013.01); *B01J 19/2465* (2013.01); *B01J 20/3014* (2013.01); *B01J 20/3078* (2013.01); *B01J 20/3085* (2013.01); *C07C 51/09* (2013.01); *C07C 51/44* (2013.01); *C07D 305/12* (2013.01); *C08F 120/06* (2013.01); *C08F 220/06* (2013.01); *C08G 63/08* (2013.01); *C08G 63/78* (2013.01); *C08G 63/83* (2013.01); *C08G 63/912* (2013.01); *C08G 81/027* (2013.01); *A01C 21/00* (2013.01); *B01J 2219/00123* (2013.01)

(58) Field of Classification Search
CPC ...... B01J 20/264; B01J 19/0013; B01J 19/06; B01J 19/245; B01J 9/2465; B01J 20/3014; B01J 20/3078; B01J 20/3085; B01J 2219/00123; A01C 1/06; A01C 21/00; A01N 25/34; A61L 15/24; B01D 3/14; C07C 51/09; C07C 51/44; C07D 305/12; C08F 120/06; C08F 220/06; C08G 63/08; C08G 63/78; C08G 63/83; C08G 63/912; C08G 81/027
See application file for complete search history.

(56) References Cited

U.S. PATENT DOCUMENTS

| | | |
|---|---|---|
| 3,800,006 A | 3/1974 | Katayama et al. |
| 6,013,590 A | 1/2000 | Noda |
| 8,445,703 B2 | 5/2013 | Allen et al. |

(Continued)

FOREIGN PATENT DOCUMENTS

| | | |
|---|---|---|
| WO | 2006131213 A1 | 12/2006 |
| WO | 2010/118128 A1 | 10/2010 |

(Continued)

OTHER PUBLICATIONS

International Search Report and Written Opinion received for PCT Patent Application No. PCT/US2017/059249, dated Feb. 22, 2018, 11 pages.

(Continued)

*Primary Examiner* — Alma Pipic
(74) *Attorney, Agent, or Firm* — Young Basile Hanlon & MacFarlane, P.C.

(57) ABSTRACT

Provided herein are absorbent polymers produced from beta-propiolactone, and methods and systems of producing such polymers. The beta-propiolactone may be derived from ethylene oxide and carbon monoxide. The absorbent polymer may be bio-based and/or biodegradable. The absorbent polymers may be used for diapers, adult incontinence products, and feminine hygiene products, as well as for agricultural applications.

36 Claims, 1 Drawing Sheet

(56) References Cited

U.S. PATENT DOCUMENTS

| | | |
|---|---|---|
| 8,796,475 B2 | 8/2014 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2011/0301027 A1 | 12/2011 | Bitis et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002385 A1 | 1/2019 | Sookraj et al. |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

International Preliminary Report on Patentability received for PCT Patent Application No. PCT/US2017/059249, dated May 16, 2019, 8 pages.

Supplementary European Search Report, dated Jun. 5, 2020, 12 pages.

Office Action in co-pending Application No. CN 201780065068.X dated Aug. 11, 2021, with English translation (15 pages).

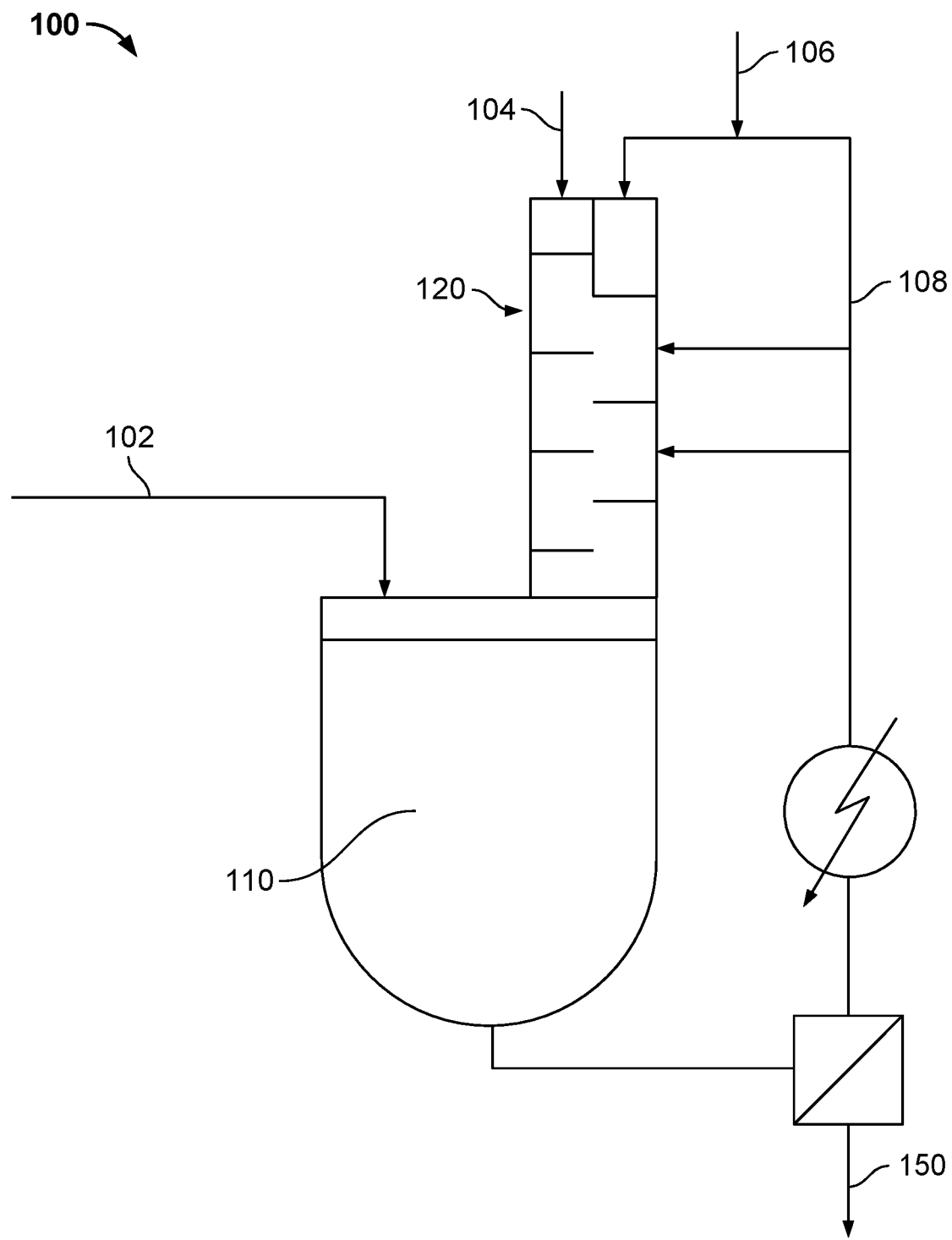

ABSORBENT POLYMERS, AND METHODS AND SYSTEMS OF PRODUCING THEREOF AND USES THEREOF

CROSS-REFERENCE TO RELATED APPLICATIONS

This application is a U.S. National Phase Patent Application under 35 U.S.C. § 371 of International Application No. PCT/US2017/059249, filed Oct. 31, 2017, which claims priority to and the benefit of U.S. Provisional Application No. 62/416,611, filed on Nov. 2, 2016, each of which is hereby incorporated by reference in its entirety.

FIELD

The present disclosure relates generally to polymeric materials, and more specifically to polymeric materials suitable for use as adsorbent materials, and methods of producing thereof.

BACKGROUND

Superabsorbent polymers are polymeric materials that can absorb and retain huge amounts of water or aqueous solutions. Such polymeric materials are used extensively for the manufacture of diapers, adult incontinence products, and feminine hygiene products, as well as well as in agricultural applications.

Superabsorbent polymers are commonly produced from polymerization of acrylic acid. However, due to volatile acrylic acid price and supply deficit, there is a desire in the art to produce polymeric materials with adsorbent properties from alternative sources. In particular, there is a need in the art to produce bio-based, bio-degradable polymeric materials with adsorbent properties, obtained from renewable sources.

BRIEF SUMMARY

Provided herein are polymeric materials with adsorbent properties, and methods of producing thereof, that addresses the need in the art. Such polymeric materials may be obtained from beta-propiolactone, which may be derived from renewable sources, such as bio-based ethylene oxide and carbon monoxide.

In some aspects, provided is a method of producing a polymer, comprising: combining beta-propiolactone with a metal compound to produce acrylic acid, a salt thereof, or a combination thereof; and polymerizing the acrylic acid, a salt thereof, or a combination thereof, with a polymerization initiator and optionally a cross-linker to produce the polymer. In some variations of the foregoing, the polymerizing is performed neat or in a non-aqueous media. In some variations, the metal compound is M, $M_2O$, MOH, or $M^+(CH_2$=$CHCOO^-)$, or a combination thereof.

In other aspects, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) increasing the temperature of the reactor to produce acrylic acid from at least a portion of the side chains in the polymer intermediate, and to produce acrylate polymer from at least a portion of the polymeric backbone of the polymer intermediate by thermolysis of the polymer intermediate;

c) adding a metal compound of formula M, $M_2O$, MOH, or $M^+(CH_2$=$CHCOO^-)$, or a combination thereof, to the reactor to at least partially neutralize the acrylic acid in the reactor to produce a mixture, wherein the mixture in the reactor comprises acrylic acid and $M^+(CH_2$=$CHCOO^-)$, wherein M is a Group I metal; and d) polymerizing at least a portion of the mixture in the reactor to produce the polymer, wherein the polymer comprises repeating units of

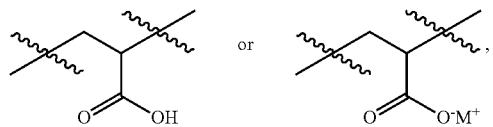

or a combination thereof.

In some variations of the foregoing, steps (c) and (d) are performed neat or in a non-aqueous media.

In other aspects, provided is a method of producing a polymer, comprising:

combining beta-propiolactone with a metal compound in a main reactor, wherein the metal compound initiates the polymerization of at least a portion of the beta-propiolactone to produce polypropiolactone in the main reactor;

thermolyzing at least a portion of the polypropiolactone in the main reactor to produce acrylic acid;

volatizing at least a portion of the acrylic acid in the main reactor;

passing the volatilized acrylic acid through a distillation column;

combining acrylic acid obtained from the distillation column with a radical initiator, optional cross-linker, and additional metal compound in a kneader reactor to produce a partially neutralized polyacrylic acid; and feeding the partially neutralized polyacrylic acid from the kneader reactor to the main reactor, wherein the carboxylate end groups of the partially neutralized polyacrylic acid initiates polymerization of at least a portion of the beta-propiolactone in the main reactor to produce a polymer with polypropiolactone branches.

In some variations of the foregoing, the polymerizing is performed neat or in a non-aqueous media.

In other aspects, provided is a polymer produced according to any of the methods described herein. In some embodiments, the polymer is cross-linked. In some variations of the foregoing, the polymer is bio-based and/or bio-degradable.

The polymers described herein, or produced according to the methods described herein, may be suitable for use as an absorbent article (e.g., for diapers, adult incontinence products, or feminine hygiene products) or as agricultural products (e.g., for agricultural materials, and seed coatings).

In yet other aspects, provided are systems for carrying out the methods described herein. In one embodiment, provided is a system, comprising: a main reactor; a distillation column connected to the main reactor; and a kneader reactor connected to the top of the main reactor via the distillation column. In another embodiment, provided is a system, comprising: a main reactor; and a vessel, comprising a distillation column and a kneader reactor, wherein the distillation column is connected to the top of the main reactor.

In some variations of the foregoing embodiments, the main reactor is configured to: receive an input stream comprising beta-propiolactone, polymerize at least a portion of the beta-propiolactone in the input stream to produce polypropiolactone, thermolyze at least a portion of the polypropiolactone to produce acrylic acid, and volatize at least a portion of the acrylic acid. In another variation, the main reactor is configured to: receive an input stream comprising beta-propiolactone, receive a mixture of a metal compound and heat transfer fluid, polymerize at least a portion of the beta-propiolactone in the input stream in the presence of the metal compound to produce polypropiolactone, thermolyze at least a portion of the polypropiolactone to produce acrylic acid, and volatize at least a portion of the acrylic acid.

In certain variations of the systems described herein, the distillation column is configured to receive the volatized acrylic acid from the main reactor. In certain variations, the distillation column is configured to receive the volatized acrylic acid from the main reactor, and feed the distilled acrylic acid to the kneader reactor.

In certain variations of the systems described herein, the kneader reactor is configured to: receive at least a portion of the acrylic acid distilled from the distillation column, receive a radical initiator, optionally a cross-linker, and a metal or metal salt, produce a partially neutralized polyacrylic acid from at least a portion of the acrylic acid in the kneader reactor, and feed at least a portion of the partially neutralized polyacrylic acid back into the main reactor. In other variations, the main reactor is further configured to: receive the partially neutralized polyacrylic acid from the kneader reactor, and polymerize beta-propiolactone to produce a polymer with polypropiolactone branches; and the main reactor further comprises an outlet configured to output a product stream comprising beta-propiolactone, the polymer and heat transfer fluid.

DESCRIPTION OF THE FIGURES

The present application can be best understood by reference to the following description taken in conjunction with the accompanying figures, in which like parts may be referred to by like numerals.

FIG. 1 depicts an exemplary system to carry out the methods described herein to produce an absorbent polymer from beta-propiolactone.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are polymers that have absorbent properties. In some aspects, such polymers are produced from beta-propiolactone. The beta-propiolactone may be produced from carbonylation of ethylene oxide. When the ethylene oxide and carbon monoxide are obtained from renewable sources, the polymers described herein may be bio-based polymers. Moreover, the polymers described herein may be biodegradable. Such superabsorbent polymers may be used for diapers, adult incontinence products, and feminine hygiene products, maintaining or improving the performance of such products.

The methods of producing such absorbent polymers, and the structure and properties of such absorbent polymers are described in further detail below.

Methods of Producing Absorbent Polymers

In some aspects, provided herein are methods of producing a polymer having a polyacrylic acid backbone and a plurality of polypropiolactone side chains, and decomposing at least a portion of the polypropiolactone side chains to produce polyacrylic acid.

In certain aspects, provided is a method of producing a polymer, comprising: combining beta-propiolactone with a metal compound to produce acrylic acid, a salt thereof, or a combination thereof; and polymerizing the acrylic acid, a salt thereof, or a combination thereof, with a polymerization initiator and optionally a cross-linker to produce the polymer. In some variations, the metal compound is a compound of formula M, $M_2O$, MOH, or $M^+(CH_2=CHCOO^-)$, or a combination thereof.

In certain aspects, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) increasing the temperature of the reactor to produce acrylic acid from at least a portion of the side chains in the polymer intermediate, and to produce acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the reactor to produce the polymer, wherein the polymer comprises repeating units of

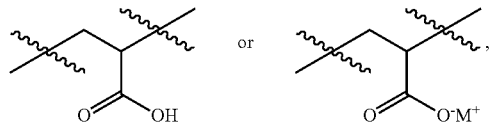

or a combination thereof.

In one variation, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) producing acrylic acid from at least a portion of the side chains in the polymer intermediate at an elevated temperature, and producing acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the reactor to produce the polymer, wherein the polymer comprises repeating units of

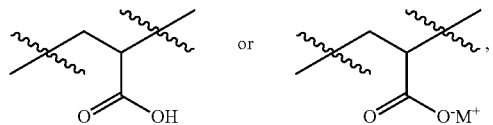

or a combination thereof.

In some variations of the foregoing, the methods further comprise isolating at least a portion of the polymer produced in step (d). In yet other variations, the methods further comprise: combining the isolated polymer with additional beta-propiolactone to produce additional polymer intermediate.

In some variations of the foregoing, the method is performed continuously.

In other variations of the foregoing, the method is performed to balance the exotherm from polymerizing beta-propiolactone to produce the polymer intermediate with the thermolysis of the polymer intermediate. For example, the heat of polymerization can be absorbed by the thermolysis of the polypropiolactone side chains, or evaporation of heat-transfer fluid, or the reaction system can be designed to allow proper temperature control.

In some variations, the method involves combining or separating some of steps (a)-(d). For example, in certain variations of the foregoing, step (c) and (d) are performed together in one step.

In yet other variations of the foregoing, steps (c) and (d) are performed neat or in a non-aqueous media.

In another aspect, provided is a method of producing a polymer, comprising: combining beta-propiolactone with a metal compound in a main reactor, wherein the metal compound initiates the polymerization of at least a portion of the beta-propiolactone to produce polypropiolactone in the main reactor;

thermolyzing at least a portion of the polypropiolactone in the main reactor to produce acrylic acid;

volatizing at least a portion of the acrylic acid in the main reactor;

passing the volatilized acrylic acid through a distillation column;

combining acrylic acid obtained from the distillation column with a radical initiator, optional cross-linker, and additional metal compound in a kneader reactor to produce a partially neutralized polyacrylic acid; and feeding the partially neutralized polyacrylic acid from the kneader reactor to the main reactor, wherein the carboxylate end groups of the partially neutralized polyacrylic acid initiates polymerization of at least a portion of the beta-propiolactone in the main reactor to produce a polymer with polypropiolactone branches.

In some variations of the foregoing aspect, the polymerization is performed neat or in a non-aqueous media. In other variations of the foregoing aspect, the method further comprises isolating a product stream from the main reactor, wherein the product stream comprises the polymer with polypropiolactone branches. In yet other variations, the product stream further comprises unreacted beta-propiolactone. In one variation that may be combined with the foregoing, the method further comprises separating a polymer stream comprising the polymer with polypropiolactone branches from a recycling stream comprising the unreacted beta-propiolactone. In yet another variation that may be combined with the foregoing, the method further comprises feeding the recycling stream into the main reactor. In the foregoing aspect and variations thereof, the radical initiator is used to polymerize acrylic acid, and there is no need to feed additional ionic initiator because the partially neutralized polyacrylic acid initiates polymerization of the beta-propiolactone.

The beta-propiolactone, the initiators and other variations of the methods are described in further detail below.

Beta-propiolactone

Beta-propiolactone may be produced by any suitable methods or techniques known in the art. For example, in some variations, beta-propiolactone is produced from ethylene oxide and carbon monoxide. The ethylene oxide undergoes carbonylation in the presence of a carbonylation catalyst and optionally a solvent.

Thus, in some variations, the methods described herein further comprise: carbonylating ethylene oxide to produce the beta-propiolactone. In certain variations, the methods described herein further comprise: combining ethylene oxide, carbon monoxide, a carbonylation catalyst and optionally a solvent to produce the beta-propiolactone. In one variation, the methods described herein further comprise: combining ethylene oxide, carbon monoxide, a carbonylation catalyst and a solvent to produce the beta-propiolactone.

The beta-propiolactone may be isolated prior to polymerization to produce the polymers described herein. Thus, in some variations, the methods described herein further comprise: carbonylating ethylene oxide to produce beta-propiolactone; and isolating at least a portion of the beta-propiolactone produced. In certain variations, the methods described herein further comprise: combining ethylene oxide, carbon monoxide, a carbonylation catalyst and optionally a solvent to produce beta-propiolactone; and isolating at least a portion of the beta-propiolactone produced. In one variation, the methods described herein further comprise: combining ethylene oxide, carbon monoxide, a carbonylation catalyst and a solvent to produce beta-propiolactone; and isolating at least a portion of the beta-propiolactone produced.

In some variations of the foregoing, the ethylene oxide is provided in gaseous form. In certain variations, gaseous ethylene oxide is converted to liquid form and combined with a solvent, a carbonylation catalyst and gaseous carbon monoxide in the reactor. In some variations of the foregoing, the carbon monoxide is provided in gaseous form.

Any suitable carbonylation catalysts may be used to produce the beta-propiolactone. For example, in some variations, the carbonylation catalyst comprises a metal carbonyl compound. In certain variations, the carbonylation catalyst is a solid-supported metal carbonyl compound. Suitable carbonylation catalysts are described in, for example, WO 2010/118128. In some variations, the carbonylation catalyst comprises [(TPP)Al] [Co(CO)$_4$], [(ClTPP)Al] [Co(CO)$_4$], [(TPP)Cr] [Co(CO)$_4$], [(C1TPP)Cr] [Co(CO)$_4$], [(salcy)Cr] [Co(CO)$_4$], [(salph)Cr] [Co(CO)$_4$], or [(salph)Al] [Co(CO)$_4$]. It should generally be understood that "TPP" refers to tetraphenylporphyrin; "C1TPP" refers to meso-tetra(4-chlorophenyl)porphyrin); "salcy" refers to (N, N'-bis(3,5-di-tert-butylsalicylidene)-1,2-diaminocyclohexane); and "salph" refers to (N, N'-bis(salicylidene)-o-phenylenediamine).

Any suitable solvents may be used to produce the beta-propiolactone. In some variations, the solvent comprises an ether solvent. In one variation, the solvent comprises tetrahydrofuran.

Ionic Initiators

In some variations, the ionic initiator comprises a salt of an alkali metal or a salt of an alkaline-earth metal. In certain variations, the ionic initiator comprises a carboxylate salt of an alkali metal, or a salt of an alkaline-earth metal. In one variations, wherein the ionic initiator is a salt of an alkali metal.

In other variations, the ionic initiator has a structure of formula $CH_2=CH_2CO_2^-Z^+$, wherein $Z^+$ is an alkali metal, ammonium, a quaternary ammonium cation, or phosphonium. In certain variations, the ionic initiator has a structure of formula $CH_2=CH_2CO_2^-Z^+$, wherein $Z^+$ is a quaternary ammonium cation. In one variation, the quaternary ammonium cation is a lower alkyl quaternary ammonium cation.

In other variations, the ionic initiator is sodium acrylate, or potassium acrylate. In certain variations, the ionic initiator is a methacrylate. In one variation, the ionic initiator is sodium methacrylate, or potassium methacrylate.

In some variations, any combinations of the ionic initiators described herein may also be used.

Metal Compound

In some variations, the metal compound is M, $M_2O$, MOH, or $M^+(CH_2=CHCOO^-)$. In certain variations, the metal compound is M, $M_2O$, or MOH. In some variations, M is a Group I metal. In certain variations, M is sodium. For example, sodium metal, sodium oxide or sodium hydroxide may be used. Any combinations of the foregoing may also be used.

Polymerization Initiators

In some embodiments, the polymerizing in step (d) of the methods described herein is performed in the presence of a polymerization initiator. Thus, in some variations, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) increasing the temperature of the reactor to produce acrylic acid from at least a portion of the side chains in the polymer intermediate, and to produce acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the reactor in the presence of a polymerization initiator to produce the polymer, wherein the polymer comprises repeating units of

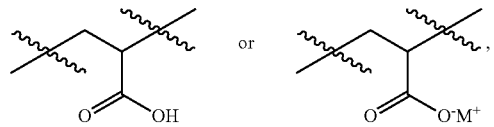

or a combination thereof.

In one variation, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) producing acrylic acid from at least a portion of the side chains in the polymer intermediate at an elevated temperature, and producing acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the presence of a polymerization initiator in the reactor to produce the polymer, wherein the polymer comprises repeating units of

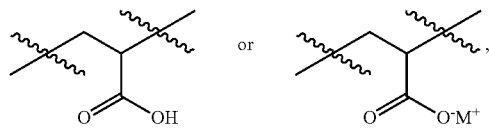

or a combination thereof.

In some embodiments, the polymerization initiator is a radical initiator. In some variations, the radical initiator comprises a peroxide, a persulfate, or an azo compound. In other variations, the radical initiator is a redox initiator. In certain variations, the radical initiator comprises a hydroperoxide. In one variation, the radical initiator comprises hydrogen peroxide.

In other embodiments, the polymerization initiator is a thermal initiator, or a photo initiator, or a combination thereof.

In some variations, the polymerization initiator is a peroxide or an acid. In one variation, the polymerization initiator is hydrogen peroxide or ascorbic acid.

In other variations, any combinations of the polymerization initiators described herein may also be used.

Cross-Linkers

In some embodiments, the methods described herein further comprise adding a cross-linker to the reactor in step (d) to polymerize at least a portion of the mixture in the reactor to produce the polymer, wherein the polymer is cross-linked. Thus, in some variations, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) increasing the temperature of the reactor to produce acrylic acid from at least a portion of the side chains in the polymer intermediate, and to produce acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the reactor in the presence of cross-linkers, and optionally a polymerization initiator, to produce the polymer, wherein the polymer comprises repeating units of

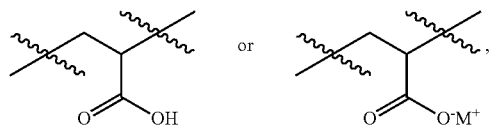

or a combination thereof, and wherein the polymer is cross-linked.

In one variation, provided is a method of producing a polymer, comprising:

a) polymerizing beta-propiolactone with an ionic initiator in a reactor to produce a polymer intermediate, wherein the polymer intermediate has a polyacrylic acid backbone and a plurality of polypropiolactone side chains;

b) producing acrylic acid from at least a portion of the side chains in the polymer intermediate at an elevated temperature, and producing acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the presence of cross-linkers, and optionally a polymerization initiator, in the reactor to produce the polymer, wherein the polymer comprises repeating units of

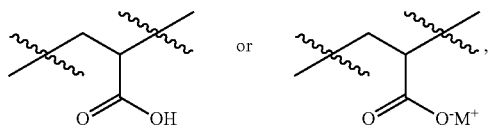

or a combination thereof, and wherein the polymer is cross-linked.

In some variations, the cross-linker is an organic compound comprising one or more vinyl groups. In certain variations, the organic compound comprises multiple vinyl groups. The cross-linkers comprising vinyl groups may radically copolymerize with acrylic acids to form a network of crosslinks. Suitable the cross-linkers may include, for example, N,N'-methylene-bisacrylamide, N,N'-ethylene-bis-methacrylamide, hexamethylene-bis-acrylamide, triallyl amine, ethylene glycol dimethacrylate, trimethylolpropane trimethacrylate, pentaerythritol trimethacrylate, and ally methacrylate. In other variations, any combinations of the cross-linkers described herein may also be used.

Systems of Producing Absorbent Polymers

Provided are also systems to carry out the methods described herein. For example, with reference to FIG. 1, system 100 is an exemplary system for producing the polymers described herein. System 100 includes reactor 110. The top of reactor 110 is connected to the distillation column portion of vessel 120, which connects reactor 110 to the kneader reactor portion of vessel 120. Various inputs are fed into vessel 120, including radical initiator and optional cross-linker 104, metal or metal salt 106, and heat transfer fluid 108. Reactor 110 has an inlet to receive beta-propiolactone stream 102, and an outlet to output product stream 150 comprising the polymers described herein.

With reference again to FIG. 1, stream 102 comprising beta-propiolactone is fed into reactor 110 containing a mixture of metal or metal salt and heat transfer fluid. The metal or metal salt initiates the polymerization of beta-propiolactone to form polypropiolactone in the reactor. Reactor 110 may be operated under suitable conditions (for example, at a temperature of 180° C. or higher) to thermolyze at least a portion of the polypropiolactone to form acrylic acid. The acrylic acid produced is volatized under the conditions in reactor 110 and distilled as it passes upwardly through the distillation column and into the kneader reaction portion of vessel 120.

A continuous feed of radical initiator, cross-linker, and metal or metal salt may be added into the kneader reactor portion of vessel 120 containing acrylic acid from the distillation column to produce cross-linked partially neutralized polyacrylic acid. The polymer produced in the kneader reactor may be continuously fed into reactor 110 via the distillation column. The carboxylate end groups on the polymer initiate the polymerization of beta-propiolactone to produce a polymer with polypropiolactone branches. The polypropiolactone chains on the polymer are thermolyzed to form acrylic acid in reactor 110.

A portion of the reaction mixture comprising beta-propiolactone, the polymer, and heat transfer fluid is flowed out of reactor 110 to form product stream 150. In other variations, product stream 150 may be separated into a polymer stream and a recycling stream comprising beta-propiolactone and the heat-transfer fluid. The recycling stream may be fed back into the kneader reactor. The separation method for the polymer may include, for example, filtration of product stream 150.

It should be understood that, in other variations, system 100 to carry out the methods described herein may have different configurations, including fewer or additional operating units to the system. Moreover, the inputs into system 100 may vary according to the methods described herein.

In some aspects, provided is a system, comprising:
a main reactor; and
a vessel, comprising a distillation column and a kneader reactor, wherein the distillation column is connected to the top of the main reactor,
wherein:
the main reactor is configured to:
receive an input stream comprising beta-propiolactone,
receive a mixture of a metal compound and heat transfer fluid,
polymerize at least a portion of the beta-propiolactone in the input stream in the presence of the metal compound to produce polypropiolactone,
thermolyze at least a portion of the polypropiolactone to produce acrylic acid, and
volatize at least a portion of the acrylic acid;
the distillation column is configured to receive the volatized acrylic acid from the main reactor, and feed the acrylic acid to the kneader reactor;
the kneader reactor is configured to:
receive at least a portion of the acrylic acid from the distillation column,
receive a radical initiator, optionally a cross-linker and a metal compound,
produce a partially neutralized polyacrylic acid from at least a portion of the acrylic acid in the kneader reactor, and
feed at least a portion of the partially neutralized polyacrylic acid back into the main reactor,
the main reactor is further configured to:
receive the partially neutralized polyacrylic acid from the kneader reactor, and
polymerize beta-propiolactone to produce a polymer with polypropiolactone branches, and
the main reactor further comprises an outlet configured to output a product stream comprising beta-propiolactone, the polymer and heat transfer fluid.

In one variation, provided is a system, comprising:
a main reactor;
a distillation column connected to the main reactor; and
a kneader reactor connected to the top of the main reactor via the distillation column,
wherein:
the main reactor is configured to:
receive an input stream comprising beta-propiolactone,
polymerize at least a portion of the beta-propiolactone in the input stream to produce polypropiolactone,
thermolyze at least a portion of the polypropiolactone to produce acrylic acid, and
volatize at least a portion of the acrylic acid;
the distillation column is configured to receive the volatized acrylic acid from the main reactor;
the kneader reactor is configured to:
receive at least a portion of the acrylic acid distilled from the distillation column,
receive a radical initiator, optionally a cross-linker, and a metal compound,
produce a partially neutralized polyacrylic acid from at least a portion of the acrylic acid in the kneader reactor, and
feed at least a portion of the partially neutralized polyacrylic acid back into the main reactor,
the main reactor is further configured to:
receive the partially neutralized polyacrylic acid from the kneader reactor, and
polymerize beta-propiolactone to produce a polymer with polypropiolactone branches, and
the main reactor further comprises an outlet configured to output a product stream comprising beta-propiolactone, the polymer and heat transfer fluid.

The systems described herein may be configured to receive beta-propiolactone provided or produced according to any of the methods described herein. For example, in some embodiments, the input stream comprising beta-propiolactone is produced by carbonylating ethylene oxide. Thus, in some embodiments, the system further comprises a carbonylation reactor configured to carbonylate ethylene oxide to produce the input stream.

In other variations, the system further comprises separation unit to isolate the polymer in the product stream. In other variations, the separation unit separates the product stream into a polymer stream and a recycling stream comprising beta-propiolactone and the heat-transfer fluid. In yet other variations, the recycling stream may be fed back into the main reactor.

The systems described herein may also be configured to receive any of the initiators, cross-linkers, and metal compounds described herein. For example, in some variations, the metal compound is M, $M_2O$, MOH, or $M^+(CH_2=CHCOO^-)$. In certain variations, M is a Group I metal. In one variation, the metal compound is sodium metal. In other variations, the metal compound is, sodium oxide, sodium hydroxide, or sodium acrylate. A combination of such metal compounds may also be used. In yet other variations of the foregoing, a cross-linker is used, and the partially neutralized polyacrylic acid produced is cross-linked. Any of the cross-linkers described herein may be used in the systems.

In other variations, the heat transfer fluid may be any aprotic organic solvent with a boiling point higher than the boiling point of acrylic acid. In one variation, the heat transfer fluid is a high boiler.

Absorbent Polymers

In some aspects, provided are polymers produced according to any of the methods described herein.

Bio-Content

In some variations of the foregoing, the polymer has a bio-content of greater than 0%, and less than 100%. In certain variations of the foregoing, the polymer has a bio-content of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%.

In some variations, bio-content (also referred to as "bio-based content") can be determined based on the following:

% Bio-content or Bio-based content=[Bio (Organic) Carbon]/[Total (Organic) Carbon]*100%, as determined by ASTM D6866 (Standard Test Methods for Determining the Bio-based Content of Solid, Liquid, and Gaseous Samples Using Radiocarbon Analysis).

The bio-content of the polymers may depend based on the bio-content of the beta-propiolactone used. For example, in some variations of the methods described herein, the beta-propiolactone used to produce the polymers described herein may have a bio-content of greater than 0%, and less than 100%. In certain variations of the methods described herein, the beta-propiolactone used to produce the polymers described herein may have a bio-content of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%. In certain variations, beta-propiolactone derived from renewable sources is used. In other variations, at least a portion of the beta-propiolactone used is derived from renewable sources, and at least a portion of the beta-propiolactone is derived from non-renewable sources.

The bio-content of the beta-propiolactone may depend on, for example, the bio-content of the ethylene oxide and carbon monoxide used. In some variations, both ethylene oxide and carbon monoxide are derived from renewable sources.

Biodegradable

In some variations of the foregoing, the polymer has a biodegradability of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%.

In some variations of the foregoing, biodegradable is as defined and determined based on ASTM D5338-15 (Standard Test Method for Determining Aerobic Biodegradation of Plastic Materials Under Controlled Composting Conditions, Incorporating Thermophilic Temperatures).

Use of the Absorbent Polymers

In other aspects, provided herein are also absorbent articles comprising the polymers described herein, or produced according to the methods described herein.

In some variations, the adsorbent article further includes at least one inorganic or organic additive. Suitable inorganic additives may include, for example, metals (such as aluminum or tin), as well as clays. The incorporation of such solids may enhance the absorbent properties of the polymer or polymer compositions. Examples of organic additives may include, for example, plasticizers such as polybutene, polypropene, polybutadiene, polyisobutene and/or polyisoprene.

In some embodiments, the absorbent article is a diaper, an adult incontinence product, or a feminine hygiene product. In some variations of the foregoing, the absorbent article is bio-based and/or biodegradable.

In certain aspects, provided is a biodegradable fabric, comprising any of the polymers described herein, or produced according to the methods described herein. In some variations of the foregoing, the biodegradable fabric further comprises at least one inorganic or organic additive.

Agricultural Uses

The polymers described herein, or produced according to the methods described herein, may also be suitable for agricultural use. In other aspects, provided is an agricultural product comprising the polymers described herein, or produced according to the methods described herein. Such agricultural product may be a material used in the planting and/or growing of plants, or a seed or a crop.

For example, the polymers described herein, or produced according to the methods described herein, may be used as agricultural materials to hold water for crops. Thus, in some variations, provided is an agricultural material comprising the polymers described herein, or produced according to the methods described herein. In certain variations, the agricultural material further includes at least one inorganic or organic additive.

In other variations, provided is a seed coated with the polymers described herein, or produced according to the methods described herein. In other embodiments, provided is a seed mix comprising seeds, wherein at least a portion of the seeds is coated with the polymers described herein, or produced according to the methods described herein. When the polymer or polymer compositions bio-degrade, water may be released.

In yet other aspects, provided is a method, comprising planting seeds, wherein at least a portion of the seeds is coated with the polymers described herein, or produced according to the methods described herein. In some variations, the method further comprises growing plants from at least a portion of the planted seeds under conditions in which the polymers bio-degrade to release water to the seeds and/or plants.

EXAMPLES

The following Example is merely illustrative and is not meant to limit any aspects of the present disclosure in any way.

Example 1

Synthesis of Absorbent Polymers

This Example demonstrates the synthesis of a polymer from beta-propiolactone (bPL).

Polymerization of bPL initiated by poly(sodium acrylate): 2 g of bPL was added to a vial containing 260 mg of poly(sodium acrylate). The reaction was run at 50° C. for 16 h. $^1$H NMR of the resulting product showed a complete consumption of bPL.

Thermolysis of PPL branched poly(sodium acrylate): The resulting product from the step above was then thermolyzed at 160° C.-180° C., and acrylic acid generated from the thermolysis was isolated by vacuum distillation. The remaining residue from the thermolysis was poly(sodium acrylate) as determined by $^1$H NMR, and the collected liquid from the vacuum distillation was confirmed to be acrylic acid by $^1$H NMR.

Synthesis of polymer from acrylic acid in neat condition: To a 40 mL scintillation vial equipped with a stir bar and a burst disk, 1.80 g of acrylic acid (Sigma Aldrich, 99%), and 0.20 g of 80% sodium oxide (Sigma Aldrich) were added at ambient temperature with stirring. Then, 0.024 g of N,N'-methylenebis(acrylamide) (99%, Sigma Aldrich) was added with stirring. The resulting mixture was then heated on a reaction block to 100° C. for 30 minutes. The solution was then purged with nitrogen via needle though the burst disk. After approximately 5 minutes of $N_2$ sparging, an exotherm by 72° C. was observed with off gassing. Heat to the vial was discontinued. The resulting solid material was ground to a fine powder with a mortar and pestle, then added to a 100 mL medium course fritted filter. The material was rinsed three times with deionized (DI) water, 50 mL each aliquot. The gel-like material was dried overnight in a vacuum oven at 105° C., yielding 0.285 g of white solid.

What is claimed is:

1. A method of producing a polymer, comprising:
   combining beta-propiolactone with a metal compound of formula M, $M_2O$, MOH, or $M^+(CH_2\!=\!CHCOO^-)$, or a combination thereof, to produce acrylic acid, a salt thereof, or a combination thereof;
   passing the acrylic acid, the salt thereof, or the combination thereof through a distillation column; and
   polymerizing the acrylic acid, a salt thereof, or a combination thereof, with a polymerization initiator and optionally a cross-linker to produce the polymer,
   wherein M is a Group I metal.

2. The method of claim 1, wherein the polymerizing is performed neat or in a non-aqueous media.

3. The method of claim 1, wherein M is sodium.

4. The method of claim 1, wherein the polymerizing is performed in the presence of a polymerization initiator.

5. The method of claim 4, wherein the polymerization initiator is a radical initiator.

6. The method of claim 5, wherein the radical initiator comprises a peroxide, a persulfate, or an azo compound, or a combination thereof.

7. The method of claim 5, wherein the radical initiator is a redox initiator.

8. The method of claim 5, wherein the radical initiator comprises a hydroperoxide.

9. The method of claim 5, wherein the radical initiator comprises hydrogen peroxide.

10. The method of claim 4, wherein the polymerization initiator is a thermal initiator, or a photo initiator, or a combination thereof.

11. The method of claim 4, wherein the polymerization initiator is a peroxide or an acid.

12. The method of claim 1, wherein the method is continuous.

13. The method of claim 1, further comprising carbonylating ethylene oxide to produce the beta-propiolactone.

14. The method of claim 1, further comprising combining ethylene oxide and carbon monoxide in the presence of a carbonylation catalyst and optionally a solvent to produce the beta-propiolactone.

15. A method of producing a polymer, comprising:
   a) polymerizing beta-propiolactone with an ionic initiator in a reactor to produce a polymer intermediate, wherein the polymer intermediate has a polyacrylic acid backbone and a plurality of polypropiolactone side chains;
   b) increasing the temperature of the reactor to produce acrylic acid from at least a portion of the plurality of polypropiolactone side chains in the polymer intermediate, and to produce acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the reactor to produce the polymer, wherein the polymer comprises repeating units of

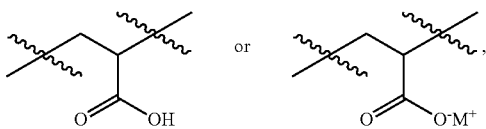

or a combination thereof.

16. The method of claim 15, wherein steps (c) and (d) are performed neat or in a non-aqueous media.

17. The method of claim 15, wherein the ionic initiator comprises a salt of an alkali metal, a salt of an alkaline-earth metal, or a combination thereof.

18. The method of claim 15, wherein the ionic initiator comprises a carboxylate salt of an alkali metal, a salt of an alkaline-earth metal, or a combination thereof.

19. The method of claim 15, wherein the ionic initiator is a salt of an alkali metal.

20. The method of claim 15, wherein the ionic initiator has a structure of formula $CH_2=CH_2CO_2^-Z^+$, wherein $Z^+$ is an alkali metal, ammonium, a quaternary ammonium cation, or phosphonium.

21. The method of claim 20, wherein the quaternary ammonium cation is a alkyl quaternary ammonium cation.

22. The method of claim 15, wherein the ionic initiator is sodium acrylate, or potassium acrylate, or a combination thereof.

23. The method of claim 15, wherein the ionic initiator is a methacrylate.

24. The method of claim 15, further comprising adding a cross-linker to the reactor in step (d) to polymerize at least a portion of the mixture in the reactor to produce the polymer, wherein the polymer is cross-linked.

25. The method of claim 15, further comprising:
isolating at least a portion of the polymer produced in step (d); and
combining the isolated polymer with additional beta-propiolactone to produce additional polymer intermediate.

26. A method of producing a polymer, comprising:
combining beta-propiolactone with a metal compound in a main reactor, wherein the metal compound initiates the polymerization of at least a portion of the beta-propiolactone to produce polypropiolactone in the main reactor;
thermolyzing at least a portion of the polypropiolactone in the main reactor to produce acrylic acid;
volatizing at least a portion of the acrylic acid in the main reactor;
passing the volatilized acrylic acid through a distillation column;
combining acrylic acid obtained from the distillation column with a radical initiator, optional cross-linker, and additional metal compound in a kneader reactor to produce a partially neutralized polyacrylic acid; and
feeding the partially neutralized polyacrylic acid from the kneader reactor to the main reactor, wherein the carboxylate end groups of the partially neutralized polyacrylic acid initiates polymerization of at least a portion of the beta-propiolactone in the main reactor to produce a polymer with polypropiolactone branches.

27. The method of claim 26, further comprising isolating a product stream from the main reactor, wherein the product stream comprises the polymer with polypropiolactone branches.

28. The method of claim 27, wherein the product stream further comprises unreacted beta-propiolactone.

29. The method of claim 26, further comprising separating a polymer stream comprising the polymer with polypropiolactone branches from a recycling stream comprising the unreacted beta-propiolactone.

30. The method of claim 29, further comprising feeding the recycling stream into the main reactor.

31. The method of claim 26, wherein the metal compound is a compound of formula M, $M_2O$, MOH, or $M^+(CH_2=CHCOO^-)$, or a combination thereof, wherein M is a Group I metal.

32. The method of claim 31, wherein M is sodium.

33. The method of claim 26, wherein the radical initiator comprises a peroxide, a persulfate, or an azo compound, or a combination thereof.

34. The method of claim 26, wherein the radical initiator is a redox initiator.

35. The method of claim 26, wherein the radical initiator comprises a hydroperoxide.

36. The method of claim 26, wherein the radical initiator comprises hydrogen peroxide.

* * * * *